United States Patent [19]

Ross

[11] Patent Number: 4,908,037
[45] Date of Patent: Mar. 13, 1990

[54] SUSPENSION PROSTHETIC SLEEVE FOR RIGOROUS ACTIVITY

[76] Inventor: Michael R. Ross, 2021 Sheridan Rd., Leucadia, Calif. 92024

[21] Appl. No.: 245,361

[22] Filed: Sep. 16, 1988

[51] Int. Cl.$^4$ .............................................. A61F 2/78
[52] U.S. Cl. ....................................... 623/32; 623/57; 02/22
[58] Field of Search .................. 2/22, 24, 311; 623/27, 623/28, 32, 33, 34, 35, 36, 57; 128/68, 75, 80 C, 80 R

[56] References Cited

U.S. PATENT DOCUMENTS

| | | | |
|---|---|---|---|
| 3,262,131 | 7/1966 | Argersinger | 623/33 |
| 3,600,717 | 8/1971 | McKeehan | 2/239 X |
| 3,874,001 | 4/1975 | Patience et al. | 2/240 |
| 3,909,855 | 10/1975 | Barredo | 623/27 X |
| 4,474,573 | 10/1984 | Detty | 128/80 C |
| 4,479,272 | 10/1984 | Beldzisky | 623/32 |
| 4,822,371 | 4/1989 | Jolly et al. | 128/80 C X |

FOREIGN PATENT DOCUMENTS

| | | | |
|---|---|---|---|
| 1560487 | 2/1969 | France | 2/311 |
| 2299846 | 9/1976 | France | 623/36 |
| 0253729 | 6/1926 | United Kingdom | 623/34 |
| 0268269 | 3/1927 | United Kingdom | 623/34 |
| 0268401 | 3/1927 | United Kingdom | 623/34 |

Primary Examiner—Werner H. Schroeder
Assistant Examiner—Sara M. Current
Attorney, Agent, or Firm—Cislo & Thomas

[57] ABSTRACT

A prosthesis sleeve for attaching a prosthesis to a partially amputated limb of the body which is made of an elastomeric material which may have a tube shape and having concentric annular ribbing on an inside surface of one end to engage the remaining portion of the limb, thereby creating a suction-type seal therebetween to suspend the prosthesis. Another end of the sleeve has a smooth inside surface which engages the prosthesis forming a seal therebetween. The combination of seals creates an air tight junction and secure attachment of the prosthesis to the limb for rigorous activity such as athletics for persons requiring prostheses.

17 Claims, 1 Drawing Sheet

SUSPENSION PROSTHETIC SLEEVE FOR RIGOROUS ACTIVITY

BACKGROUND OF THE INVENTION

This invention relates generally to a prosthetic sleeve for attaching a prosthesis to a remaining portion of a human limb which was either amputated or deformed. More particularly, the invention relates to sleeves for obtaining durable engagement between a leg which has been amputated below the knee and a complementary leg or foot prosthesis. However, the sleeve has other applications in the prosthesis area.

A preliminary patent search was conducted at the Patent and Trademark Office and was directed to the field of search encompassing Classes D24/33, 128/68, 75, 80C, 80R, 623/27, 28, 32, 33, 34, 35 and 57.

Listed below are the following patents uncovered by the search.

| Patent No. | Inventor | Issue Date |
|---|---|---|
| 112,683 | S. F. Burd, et al. | March 14, 1871 |
| 1,032,074 | G. E. Marks | July 9, 1912 |
| 1,632,277 | C. Desoutter | June 14, 1927 |
| 2,080,003 | E. Blevens | May 11, 1937 |
| 2,152,141 | T. Kohl | March 28, 1939 |
| 2,545,146 | R. R. Hydorn | March 13, 1951 |
| 3,262,131 | S. Argersinger | July 26, 1966 |
| 3,600,717 | L. McKeehan | August 24, 1971 |
| 3,909,855 | J. G. Barredo | October 7, 1975 |
| 4,479,272 | D. Beldzisky | October 30, 1984 |

A more detailed description of the more pertinent patents follows. Numerals cited refer to the specification of that patent discussed.

The Argersinger (U.S. Pat. No. 3,262,131) is directed to an artificial leg with a detachable stump and supporting sock. A truncated sleeve 1 has two leg bars 2 secured to opposite sides and having a downwardly stump receiving member 6 which is also of a hollow truncated shape sized to fit wedgedly within the upper end of the sleeve 1. A knitted stump sock member 9 is also incorporated. The patent discloses a modification of the interior of the sleeve 12 having series of angularly arranged inwardly and downwardly projecting teeth or catches 14 which are designed to grip or engage the side of the stump side 9 and prevent withdrawal of the stump side.

The Beldzisky (U.S. Pat. No. 4,479,272) is directed to a sheath for retaining a prosthesis to a portion of a limb. The prosthesis 11 is retained by a sheath 17 formed of elastic material and having a welt 24 at the edge of its upper opening.

The Barredo Pat. No. (3,909,855) is directed to a prosthesis for a below-the-knee amputee. The prosthesis 10 is fitted with concave side extensions 11 which are sufficiently resilient to grip the sides of the knee sufficiently to hold the prosthesis in place. The front portion 12 is cut away to prevent contact with the patella. In an alternative embodiment, an elastic strap 20 may be provided to pass around the front of the leg just above the knee cap, coupling the opposing side portions 11 together.

The Hydorn (U.S. Pat. No. 2,545,146) is directed to a leg prosthesis having inflatable means to assist in supporting the weight of the wearer. The prosthesis is coupled to the stump by means of a leather boot 2 hingedly coupled to the lower leg portion. The boot 2 is laced together and is not provided with ribs for retention to the natural limb.

The Kohl (U.S. Pat. No. 2,152,141) is directed to a knee strap for retention of a prosthesis. The retention device 5 includes a front knee cap covering portion 6 having a rolled lower edge 7 and a pair of extending elastic straps 19 for coupling to the prosthesis 20. The strap 5 is retained to the limb 25 by a buckle 9.

The Blevens (U.S. Pat. No. 2,080,003) is directed to a support for a leg prosthesis. The strap like retaining device 1 includes a pair of supporting straps 2 which fasten to the prosthesis 5. The belt 1 is provided with a buckle 1a which is fastened above the knee with both retaining straps 2 being angularly directed to leave an opening for the knee.

The above prior art devices provide ways to secure a leg prosthesis, however do not allow rigorous athletic activities. Movement or positioning between the stump and prosthesis results. The connection is not secure enough for rigorous activity and such movement creates instability, frictional heat and abrasions.

Additionally, prosthetic rubber knee sleeves are currently sold made of latex or neoprene. The sleeves have various layers for comfort and range over a variety of sizes and configuration for greater comfort and flexibility. These sleeves must be pulled up around the stump sufficient to allow the inside surface of the sleeves to frictionally engage the flesh. Positioning occurs between the stump and the prosthesis creating friction and heat leading to painful blisters, in certain instances depending on one's activity level.

Often times, conventional sleeves must be pulled way up on the stump which can be uncomfortable to obtain sufficient engagement with the prosthesis for rigorous activity, such as running, tennis, basketball, etc.. A greater amount of skin surface must be in contact with the sleeve, which is not only uncomfortable, but unhealthy for the skin. Furthermore, the fleshy part of the thigh changes shape and size over the course of its range of motion and during rigorous activity.

There is great interest in the handicapped community for prosthetic sleeves which are durable, waterproof, provide secure engagement, allow rigorous activity, and are easily worn, yet comfortable.

The features identified above as being desirable for prosthetic sleeves are all provided by the present invention.

SUMMARY OF THE INVENTION

The present invention is embodied in a prosthetic knee sleeve for retaining a prosthesis to a remaining portion of the limb proximal to the nearest joint, known as the residual limb. The sleve comprises a closed cell elastomeric sleeve of a diameter equal to or less than the circumference of the residual limb. The sleeve has a first end which may be stretched around the prosthesis and engage the prosthesis creating a seal therebetween. The sleeve has a second end defining a plurality of uninterrupted annular ribbing on an inside surface of the sleeve. The second end of the sleeve may be stretched around the residual limb so that the ribbing engages the limb, thereby creating a seal. A suction is created between the two seals preventing the stump from pulling away from the prosthesis or vice-versa and pistoning within. Only a certain amount of movement will occur due to the natural elasticity of skin.

DESCRIPTION OF THE PREFERRED EMBODIMENT

Figure 2:
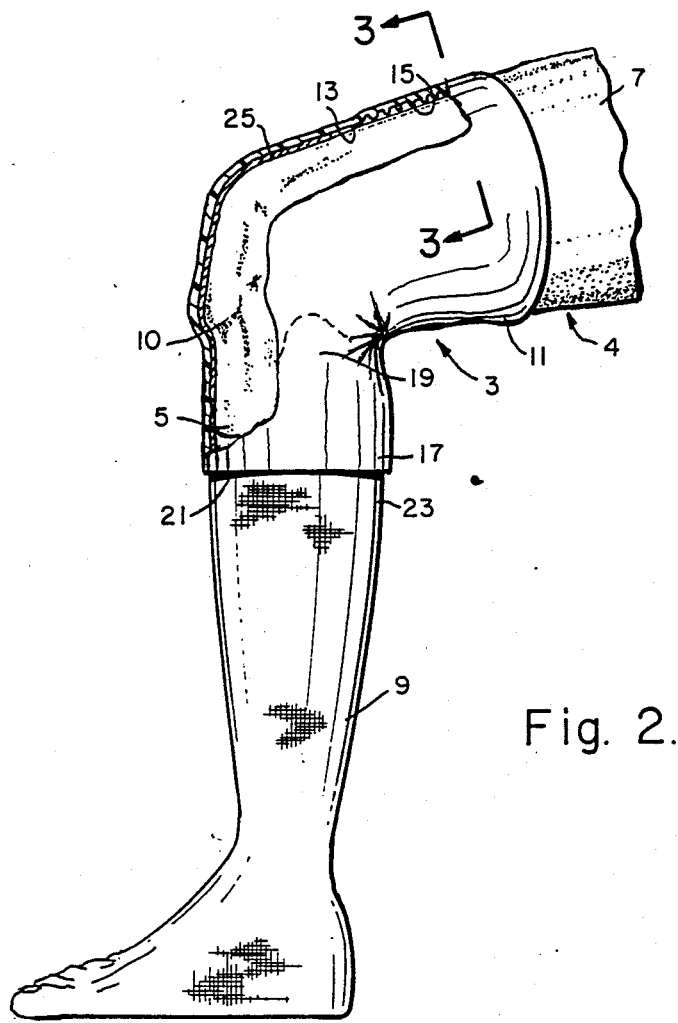
FIG. 2 is a perspective view of the suspension prosthetic sleeve of the claimed invention shown engaging a limb and a prosthesis with a portion of the sleeve shown cut away and in crossection.
Figure 1:
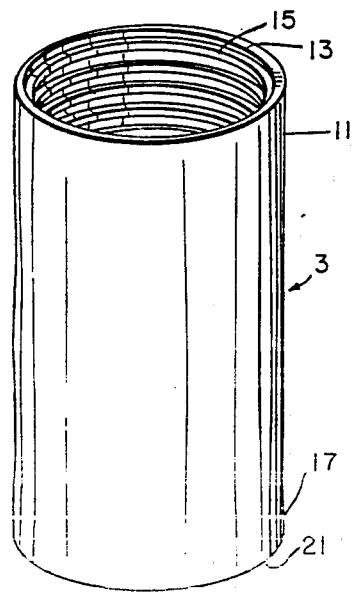
FIG. 1 is a perspective view of the suspension prosthetic sleeve of the claimed invention.
Figure 3:
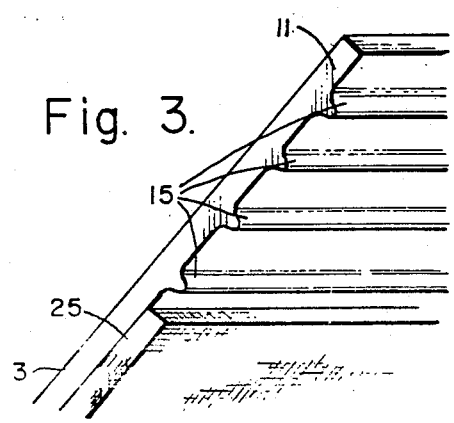
FIG. 3 is an enlarged and partial crossectional view of the suspension prosthetic sleeve of the claimed invention shown engaging a below the knee prosthesis and an intact thigh section taken along lines 3—3.

As shown in FIGS. 1-3, the invention is embodied in a prosthetic knee sleeve 3 shown engaging a residual limb 4 of a leg or thigh 7 and a calf and foot prosthesis 9. Residual limb 4 refers to the stump portion including above the knee. The portion of the leg closest to the amputation, but below the remaining joint is generally termed a stump 5. The sleeve is made of a closed cell elastomeric material, preferably a heavy latex to withstand tearing or wear under rigorous activity. The sleeve 3 allows twisting and flexing movement and retains the prosthesis by atmospheric suspension. In the preferred embodiment a natural rubber is used which is more comfortable.

On a first end 11 formed on an inside surface 13 is a plurality of uninterrupted annular and concentric ribbing 15. The first end 11 is of a disameter equal to or less than the residual limb 4. The ribbing 15 is similarly made of an elastomeric material. The ribbing 15 mechanically engages the flesh of the thigh 7 creating slight indentations or ripples between each of the plurality of ribbings. These indentations are visible on the skin upon removal of the sleeve 3. They disappear in minutes depending upon how tight the sleeve is worn and the blood circulation of the wearer. A seal is created between the stump 5 and the first end 11 of the sleeve 3, which is air and water tight. A frictional seal alone may be insufficient to securely hold the prosthesis 9 for rigorous activity because the thigh 7 is fleshy and fluctuates in size over the course of a day, and changes its fleshy shape when flexed and relaxed through the normal range of motion, especially depending on where the sleeve is worn on the thigh 7.

Although the ribbing 15 also frictionally engages the flesh like prior art knee sleeves, it is the ribbing 15 which creates a superior engaging surface contact so that the actual surface area of contact between the sleeve 3 and the thigh 7 can be vastly reduced. The sleeve 3 can be worn much lower on the thigh 7 than conventional sleeves. The exposed skin in contact with the sleeve 3 is substantially reduced and less sleeve/skin abrasion can be expected during rigorous physical activity, as heat can be dissipated offering greater comfort.

The ribbing 15 preferably has rounded edges and each of the plurality of ribbing 15 has a depth between 1/32 (one-thirty-seconds) and 1/16 (one-sixteenth) of an inch. Ribbing which is any deeper may prove irritative to the skin. Ribbing which is shallower may not engage the skin sufficiently to create the necessary seal. Each of the plurality of ribbing 15 is spaced approximately ⅛ (one-eighth) inch apart. It is believed that good results can occur using at least three of each of the plurality of ribbing 15. However, in the preferred embodiment, the above described ribbing 15 usually exceeds three ribs and the ribbing 15 covers an axial length of the sleeve 3 of about two inches. A cross-hatched type knurling, suction cups, and stipples, not shown, may possibly work as well to achieve the same sealing effect as the ribbing 15. Use to date has not been proven as effective as ribbing 15.

In one embodiment of the present invention the ribbing 15 rises 5 to 20 1000th's of an inch above the inside surface of the sleeve 3 and has proven effective.

Using the plurality of ribbing 15 the holding capability of the sleeve 5 is increased dramatically for the ratio of skin contact. Persons wearing applicant's invention can actually hang upside down by the prosthesis alone due to the holding power and engagement created by the unique ribbing 15 of applicant's invention.

The elasticity of the sleeve 3 allows stretching as the knee is flexed. Like a rubber band, the sleeve 3 can return to its unstretched shape. This action helps to extend the prosthesis 9 aiding knee extension. This extension assistance is achieved without the use of a supplemental elastic strap, as the sleeve's elasticity longitudinally is utilized.

Part of the securement of the stump 5 to the prosthesis 9 results from a vacuum-type seal created between the ends 11 and 17 of the sleeve. The seal is both water and air tight. As such, the sleeve 3 could be used for swimming prosthesis also. The ribbing 15 creates a seal allowing adequate suspension for everyday walking or running with the sleeve 3 worn lower on the thigh 7, which is cooler since less skin surface must be in contact with the sleeve 3.

An air tight seal is created at the first end 11 of the prosthesis 9 and a second end 17 of the sleeve 3. The second end 17 of the sleeve is designed to have a diameter of less than or equal to the diameter of a joining portion 19 of the prosthesis 9. The joining portion 19 has a smooth exterior surface 23. An inside surface 21 of the second end 17 of the sleeve 3 is also smooth which complements the smooth surface 23 of the joining portion 19 of the prosthesis 9. As such, frictional engagement occurs, while also creating an air and water tight seal between the joining portion 19 of the prosthesis 9 and the second end 17 of the sleeve 3. A securing band, not shown, may also be used to insure a durable attachment to create a seal between the sleeve 3 and the joining portion of the prosthesis 9. The band cinches around the sleeve 3 and the joining portion 19 and is helpful when the sleeve may be oversized for the prosthesis or if the joining portion 19 has a rough finish.

The invention can be embodied in a variety of different types of sleeves. The diameter of the first and second ends 11 and 17 can vary depending upon the size of the person's thigh 7 who will be wearing the sleeve 3 and the size of the prosthesis 9. Also, the length of the sleeve 3 can be varied for different sized wearers. The sleeve's thickness may vary along its length. At the first end 11 the sleeve is thickest for durability, while at the sleeve's second end 17, the sleeve 3 is thinner. The thick end 11 may be 55-73 1000th's of an inch while the thinner end 17 may be 8 to 10 mills thinner at 55-63 1000th's of an inch. The sleeve 3 can flex easier where it is thinner and durability is not as critical. Thickness may be critically determined to offer a proper trade-off between comfort and durability. The sleeve 3 is formed using a dipping process which results in a sleeve 3 without seams that reduces the possibility of tearing. The lack of a seam also adds to the comfort of the sleeve 3.

The sleeve 3 must be durable enough not to rip, suffer a puncture or abrasion which breaks the atmospheric seal. Such breaks can occur from improperly finished edges of prostheses or other coarse surfaces in contact with the sleeve 3. The sleeve 3 may still offer some suspension if ruptured, but only if worn much higher on the thigh 7 and is less effective as is other sleeves which offer only circumferential tension.

Other embodiments of the invention are formed with bends, enlarged sections or portions for purposes of allowing greater flexibility at specifically designed points along the sleeve's length.

However, a tubular design as shown in FIG. 1, wherein the diameter of the sleeve is constant and concentric around the sleeve's axial length provides the wearer greatest flexibility in wearing the sleeve 3. The sleeve 3 can be easily pulled up around the thigh 7 or down the thigh 7 as desired. One size can fit a larger number of wearers which reduces the amount of different sizes that need to be made available.

The sleeve 3 can be worn with most conventional stump socks 25 as shown in FIG. 1. The sock 25 may be worn just below the sleeve's ribbing 15 to allow added comfort and further minimize the total skin surface area which must come in contact with the sleeve 3, and yet insure proper engagement. The sock 25 absorbs moisture and heat away from the stump 5 or thigh 7 to prevent chaffing and abrasion. Socks 25 should be worn at least one to two inches above one's patella 10, but at least one inch lower than the ribbing 15, but preferably two inches so that the ribbing 15 is fully engaging.

To properly don the sleeve 3, the wearer puts on his stump sock 25 over his stump 5. The second end 17 of the sleeve 3 is properly fitted around the joining portion 19 of the prosthesis 9. The end 17 is stretched over the top of the prosthesis 9 and pulled down to grip the prosthesis 9. The first end 11 is folded over the second end 17 which grips the joining portion 19 of the prosthesis 9. The stump 5 and stump sock 25 is placed on top of the prosthesis 9 which may define a receiving recess. The sleeve 3 is pulled up around the stump 5 and sock 25, up to a position so that the ribbing 15 can engage the skin of the thigh 7. The wearer can use talcum powder applied to the outside surface of the sleeve 3. The talcum powder serves as a dry lubricant making it easier to pull the sleeve 3 over itself when donning and doffing the sleeve 3. In the preferred embodiment, the sleeve 3 can be treated with a chlorine solution to create a slippery surface and allow the donning and doffing of the sleeve 3 easily without the use of talcum powder.

The ribbing 15 is pulled just over the sock 25 so that the ribbing 13 can engage the skin of the thigh 7. It is easiest to fold the ribbing portion of the sleeve 3 back over itself before pulling the sleeve 3 up so that the ribbing 13 does not prematurely engage the skin. The sleeve 3 ideally should be worn three to four inches above the top of one's patella 10. If the sleeve 3 is too tight, the sleeve 3 should be moved down to two to three inches above the patella 10 or use a larger sized sleeve. If the sleeve is too loose a smaller sized sleeve should be chosen. The sleeve 3 should be adjusted so that no wrinkles are present which could cause skin irritation.

The wearer can adjust how high he or she wishes to wear the sleeve 3 for added comfort or support. The sleeve 3 should be worn higher up on the thigh 7 for added support. Garters to retain the sleeve are not necessary since the ribbing 15 maintains the sleeve's position on the thigh 7 once it has been properly put on. In the event the natural elasticity of the sleeve 3 decays over an extending period of time or use, the sleeve 3 can be worn higher on the thigh 7, possibly six inches above the patella 10, depending upon the tension necessary to create a good seal.

For doffing or taking the sleeve 3 off, the ribbing portion of the sleeve 3 is folded back over itself to help break the seal. Then, the sleeve 3 is peeled off the thigh 7 and prosthesis 9. When removing the stump 5 from the prosthesis 9, the sleeve 3 is folded down from the thigh 7 over the top of the prosthesis 9 and allows separation of the stump 5 from the prosthesis 9. The sleeve 3 should be pulled back up to its extended condition so as not to stretch out over time.

Of course, there are a number of different ways to don or doff the sleeve of the present invention not herein recited, but prevalently described by the prior art which may be applicable herein.

A number of different types of interior or exterior surfaces for the sleeve 3 may be utilized, so long as the suction-type seal between the first and second ends 11 and 17 are maintained. This suction-type seal further prevents pistoning movement between the prosthesis 9 and the stump 5, which is common with most other types of suspension systems. Since both ends 11 and 17 of the sleeve 3 create an air tight seal, a vacuum is created whenever the prosthesis 9 is pulled away from the stump 5. It is thought that a closed cell neoprene can also be used and achieve the effect of applicant's invention. However, the seal is short-lived compared to latex.

Interestingly, the sleeve 3 of the present invention has other orthopedic applications in conjunction with non-prosthetic devices. The sealing effect of the ribbing 15 allows a seal to be formed between the thigh and another orthopedic support. Therefore, the invention is not limited to prosthetic applications. Both knee and elbow braces are possible applications, possibly using a plurality of ribbing on each end of the sleeve.

It should be appreciated from the foregoing description that the present invention provides a improved prosthetic sleeve for active wear by amputees. The sleeve is durable, provides substantial support, is comfortable to wear and creates a position suction seal between the thigh and the prosthesis. The sleeve can be easily made and fit a variety of different people with a great degree of adjustability while maintaining the effects of atmospheric suspension.

Although the present invention has been described in detail with reference only to the presently preferred embodiments, it will be appreciated by those of ordinary skill in the art that various modifications can be made without departing from the invention. Accordingly, the invention is limited only by the following claims.

I claim:

1. A prosthetic sleeve for retaining a prosthesis to a residual limb, comprising:

a sleeve of a diameter equal to or less than the circumference of the limb made of an air impermeable elastomeric material, further comprising a first end of said sleeve which may be stretched around the prosthesis and engage the prosthesis creating a substantially air tight seal therebetween, and comprising a second end of said sleeve defining an irregular and continuous inside surface means for sealing said sleeve, wherein said second end may be stretched around the limb so that said irregular and continuous surface means positively and mechanically displaces skin of the limb creating a substantially air tight seal sufficient to retain the limb to the prosthesis by atmospheric pressure.

2. A prosthetic sleeve is claimed in claim 1, wherein said sleeve is of a uniform diameter and a sufficient length to engage the limb and the prosthesis maintaining said substantially air tight seal, and wherein said surface means is defined by a plurality of annular ribbing.

3. A prosthetic sleeve as claimed in claim 2, wherein said sleeve is concentric with its axial length.

4. A prosthetic knee sleeve as claimed in claim 1, wherein said second end of said sleeve is of a larger diameter than said first end of said sleeve, and wherein said surface means is defined by a plurality of annular ribbing.

5. A prosthetic knee sleeve as claimed in claim 1, wherein said sleeve is formed with a bend of a predetermined degree between said first and said second ends allowing for a specific point of flexing.

6. A prosthetic sleeve as claimed in claim 5, wherein said second end of said sleeve is of a larger diameter than said first end of said sleeve, and wherein said surface means is defined by a plurality of annular ribbing.

7. A prosthetic sleeve for rigorous activity allowing a wearer of a prosthesis active use of his or her residual limb in conjunction with the prosthesis, comprising:
  an air impermeable elastomeric band having formed on an inside surface of one end a plurality of ridges indenting skin of the limb when said band is worn over the limb, said band having an opposite end which may be worn over the prosthesis, wherein the limb is secured to the prosthesis by atmospheric pressure as a substantially air tight seal between the skin of the limb and the prosthesis is created.

8. A prosthetic sleeve as claimed in claim 7, wherein said one end of said band is of a larger diameter than said other end of said band.

9. A prosthetic sleeve as claimed in claim 8, wherein said band has a bend of a predetermined degree between said one end and said other end to allow greater flexing at said bend.

10. A prosthetic sleeve as claimed in claim 7, wherein said band is of a uniform diameter and of a sufficient length to engage the limb and the prosthesis when worn.

11. A prosthetic sleeve as claimed in claim 7, wherein said ridges are concentric with said band's axial length.

12. A prosthesis sleeve as claimed in claim 11, wherein said ridges are annular and uninterrupted so as to provide said substantially air tight seal between said band and the limb when properly worn.

13. A prosthesis knee sleeve to retain a residual limb or stump to a below-the-knee prosthesis for rigorous activities, comprising:
  an air impermeable elastomeric sleeve of a diameter equal to or less than the circumference of the limb to be held, said sleeve having a first end defining an inside surface having a plurality of uninterrupted annular ribbing concentric with the axial length of said sleeve, wherein said first end of said sleeve may be stretched over the thigh, said ribbing mechanically engaging skin of the limb so as to create a substantially air tight seal therebetween, and wherein said sleeve having a second end defining a smooth inside surface which may be stretched over the prosthesis, engaging the prosthesis so as to create a substantially air tight seal therebetween, creating an air tight connection between the skin of the limb and the prosthesis and keeping the prosthesis firmly engaged to the limb by atmospheric pressure.

14. A prosthetic knee sleeve as claimed in claim 13, wherein said sleeve is of a uniform diameter and a length sufficient to engage the limb and the prosthesis.

15. A prosthesis knee sleeve as claimed in claim 14, wherein said sleeve is concentric with its axial length.

16. A prosthetic knee sleeve as claimed in claim 14, wherein said sleeve is formed with a bend of a predetermined degree between said first and second ends, allowing for a point of flexing.

17. A prosthesis knee sleeve as claimed in claim 14, wherein the thickness of said ribbing is roughly between 1/32 (one-thirty-seconds) to 1/16 (one-sixteenth) of an inch, the plurality of ribbing comprising three or more, and each of said plurality of ribbing being spaced at least about 1/8 (one-eighth) of an inch apart.

* * * * *